(12) United States Patent
Miyata et al.

(10) Patent No.: US 7,718,763 B2
(45) Date of Patent: May 18, 2010

(54) SUBSTRATE POLYEPTIDES FOR VON WILLEBRAND FACTOR CLEAVING PROTEASE ADAMTS-13

(75) Inventors: Toshiyuki Miyata, Suita (JP); Koichi Kokame, Ibaraki (JP)

(73) Assignee: Japan as Represented by the President of National Cardiovascular Center, Suita-Shi, Osaka (JP)

( * ) Notice: Subject to any disclaimer, the term of this patent is extended or adjusted under 35 U.S.C. 154(b) by 416 days.

(21) Appl. No.: 10/531,427

(22) PCT Filed: Oct. 18, 2002

(86) PCT No.: PCT/JP02/10816

§ 371 (c)(1),
(2), (4) Date: Apr. 15, 2005

(87) PCT Pub. No.: WO2004/035778

PCT Pub. Date: Apr. 29, 2004

(65) Prior Publication Data

US 2007/0065895 A1    Mar. 22, 2007

(51) Int. Cl.
*A61K 38/00* (2006.01)
*A01N 37/18* (2006.01)
*C08H 1/00* (2006.01)
*C12P 21/04* (2006.01)

(52) U.S. Cl. ..................... 530/300; 530/350; 530/402; 435/13

(58) Field of Classification Search ........................ None
See application file for complete search history.

(56) References Cited

U.S. PATENT DOCUMENTS 5,849,536 A * 12/1998 Garfinkel et al. ........... 435/69.6

OTHER PUBLICATIONS

Girma et al. (1986) Blood, vol. 67, pp. 1356-1366.*
Kokame et al. (E. publication of Sep. 25, 2003) Blood, vol. 103, pp. 607-612.*
Wu et al., Characterization of a core binding site for ADAMTS-13 in the A2 domain of von Willebrand factor., PNAS, 2006, vol. 103, pp. 18470-18474.*
Definition of "Coupling agent", obtained from composite.about. com/od/glossaries/l/bIdef_c1324.htm, last veiwed on Sep. 10, 2009.*
Remuzzi et al., "Von Willebrand factor cleaving protease (ADAMTS13) is deficient in recurrent and familial thrombotic thrombocytopenic pupura and hemolytic uremic syndrome", Blood, Aug. 2002, vol. 100, No. 3, pp. 778-785.
Verweji et al., "Full-length von Willbrand factor (vWF) cDNA encodes a highly repetitive protein considerably larger then the mature vWF subunit", EMBO J, 1986, vol. 5, No. 8, pp. 1839-1847.
Jenkins et al., "Molecular modeling of ligand and mutation sites of the type A domains of human von Willebrand factor and their relevance to von Willebrand's disease", Blood, 1998, vol. 91, No. 6, pp. 2032-2044.
He et al., "Are increased levels of von Willebrand factor in chronic coronary heart disease caused by decrease in von Willebrand factor cleaving protease activity? A study by an immunoassay with antibody against intact bond 842Tyr-843Met of the von Willebrand factor protein", Thromb Res., 2001, vol. 103, No. 3, pp. 241-248.
Hyland et al., "A radiometric assay for HIV-1 protease", Anal Biochem., 1990, vol. 188, No. 2, pp. 408-415.

* cited by examiner

*Primary Examiner*—David J Steadman
*Assistant Examiner*—Alexander D Kim
(74) *Attorney, Agent, or Firm*—Birch, Stewart, Kolasch & Birch, LLP

(57) ABSTRACT

The present invention relates to specific substrates for a von Willebrand factor cleaving enzyme, ADAMTS-13, as well as to diagnosis of ADAMTS-13 deficient patients, diagnostic compositions, and kits employing the substrates. Particularly preferable substrate polypeptides for ADAMTS-13 are the polypeptide which begins at amino acid 1587 and ends at amino acid 1668 of SEQ ID NO: 1 in the Sequence Listing, and the polypeptide which begins at amino acid 1596 and ends at amino acid 1668 of SEQ ID NO: 1 in the Sequence Listing. These substrate polypeptides for ADAMTS-13 have high substrate specificity and also superior quantitativeness, and a suitable size for production by recombinant methods.

19 Claims, 2 Drawing Sheets

SUBSTRATE POLYEPTIDES FOR VON WILLEBRAND FACTOR CLEAVING PROTEASE ADAMTS-13

TECHNICAL FIELD OF THE INVENTION

The invention relates to a specific substrate for enzymes cleaving plasma proteins, in particular, von Willebrand factor, a method for assaying activity thereof, and a high throughput system for assaying enzymatic activity of cleaving von Willebrand factor.

PRIOR ART

Von Willebrand factor (hereinafter referred to as "VWF") is a plasma protein which plays a significant role in the blood coagulation. VWF is synthesized mainly in vascular endothelia and released into the bloodstream in multimeric forms of high molecular weights. Normally, VWF undergoes limited cleavage to forms of appropriate sizes by a von Willebrand factor cleaving enzyme (designated as ADAMTS-13 or VMF-CP, hereinafter referred to as "ADAMTS-13") in the plasma, and accordingly its activity of accelerating the coagulation is regulated. Significant decrease in the activity of ADAMTS-13 causes abnormal polymerization of VWF. As a result, thrombi which result particularly from excess aggregation of thrombocytes are formed, leading to a severe systemic disease called thrombotic thrombocytopenic purpura (hereinafter referred to as "TTP"). TTP is broadly classified into congenital and acquired types.

Recently, ADAMTS-13 has been isolated, and its coding gene ADAMTS13 has been identified[1]. Mutation in this gene will be responsible for congenital TTP, whereas there is elucidated no mechanism of developing acquired TTP which accounts for the majority of TTP and is induced by pregnancy, side effects of drugs, and others.

TTP, which is a thrombotic systemic disease involving thrombocytopenia, will most likely lead to death, if left untreated. After the effectiveness of plasma exchange has become to be known, the fatality rate has been remarkably reduced. However, plasma exchanging once in every two to three weeks imposes heavy burdens on patients, and also risks such as infections are not negligible. Thus, there is a need for accurate and rapid measuring of ADAMTS-13 activity make an accurate judgment of the timing of plasma exchange, thereby to reduce the number of plasma exchanging and to increase therapeutic effects. In addition, accurate measuring of ADAMTS-13 activity is indispensable for the prediction of acquired TTP. Accurate measuring of ADAMTS-13 activity allows one to obtain clinical information that the activity is not decreased, that is, no sign of developing TTP appears, by periodically measuring the activity of ADAMTS-13 in the blood, for example, during taking drugs that have side effects of developing TTP, and during the pregnancy tending to induce TTP. It is also possible to make a definite diagnosis of patients with TTP, based on the decrease in ADAMTS-13 activity.

As a disease which displays clinical symptoms closely similar to TTP, there is known HUS (hemolytic uremic syndrome). In patients with HUS, however, the activity of ADAMTS-13 is in normal levels, which is contrast to the decrease or loss of ADAMTS-13 activity in TTP patients. Therefore, accurate measuring of the ADAMTS-13 activity of patients also allows one to make a discrimination between TTP and HUS.

ADAMTS-13 specifically cleaves the peptide bond between $Tyr^{1605}$-$Met^{1606}$ of the VWF subunit[2]. It is not known that enzymes other than ADAMTS-13 specifically cleave this site. At present, there are known methods for measuring ADAMTS-13 activity, such as (i) combinations of electrophoresis and western blot of reaction solutions using purified VWF as the substrate[3], (ii) measurement of the ability of VWF to bind to collagen[4], (iii) quantitative determination using VWF site-specific monoclonal antibodies[5]. However, these methods have disadvantages, for example, of requiring much time and skill for their operation, lacking the quantitativeness, and having low sensitivity, and also lack the simplicity and the capability of processing many samples, making it difficult for them to become used widely in the clinical field. In addition, it is said that it is impossible in the case of ADAMTS-13, due to the problem of the substrate specificity, to utilize chromogenic or fluorescent synthetic peptide substrates which are commonly used as high throughput systems for assaying of protease activities[6].

PROBLEMS TO BE SOLVED BY THE INVENTION

Although TTP caused by reduced activities of ADAMTS-13 is a very severe disease, as mentioned above, the current situation is that no method for accurate and rapid measuring of ADAMTS-13 activity has yet been established. Therefore, the present invention is intended to overcome the shortcomings of conventional methods for measuring ADAMTS-13 activity, thereby contributing to effective treatments of TTP, making a prediction of developing TTP, a definitive diagnosis of TTP, a discrimination between TTP and HUS, and others.

MEANS FOR SOLVING THE PROBLEMS

In view of the above-described situation, the inventors have conducted extensive research, and have found that ADAMTS-13 specifically cleaves terminally cleaved, relatively short partial amino acid sequences, or even mutant sequences thereof, of the mature VWF subunit, which contain the cleavage site that is between the 1605th amino acid tyrosine and the 1606th amino acid methionine of the amino acid sequence of wild-type human VWF depicted in SEQ ID NO: 1 (hereinafter, also expressed as $Tyr^{1605}$-$Met^{1606}$, and sometimes simply referred to as the "cleavage site"), resulting in successful measurement of ADAMTS-13 activity in a simple, specific, sensitive, and quantitative manner, thereby reaching the completion of the present invention.

Therefore, the present invention provides:

(1) a substrate polypeptide for ADAMTS-13, which begins at one of amino acids 764 to 1605 and ends at one of amino acids 1606 to 2813 of the amino acid sequence of wild-type human VWF depicted in SEQ ID NO: 1 in the Sequence Listing, wherein the polypeptide beginning at amino acid 764 and ending at amino acid 2813 of SEQ ID NO: 1 of the Sequence Listing is excluded;

(2) a substrate polypeptide for ADAMTS-13, which begins at one of amino acids 1459 to 1605 and ends at one of amino acids 1606 to 1668 of the amino acid sequence of wild-type human VWF depicted in SEQ ID NO: 1 in the Sequence Listing;

(3) a substrate polypeptide for ADAMTS-13, which begins at one of amino acids 1459 to 1600 and ends at one of amino acids 1611 to 1668 of the amino acid sequence of wild-type human VWF depicted in SEQ ID NO: 1 in the Sequence Listing;

(4) a substrate polypeptide for ADAMTS-13, which begins at one of amino acids 1554 to 1600 and ends at one of amino acids 1660 to 1668 of the amino acid sequence of wild-type human VWF depicted in SEQ ID NO: 1 in the Sequence Listing;

(5) a substrate polypeptide for ADAMTS-13, which begins at amino acid 1587 and ends at amino acid 1668 of the amino acid sequence of wild-type human VWF depicted in SEQ ID NO: 1 in the Sequence Listing;

(6) a substrate polypeptide for ADAMTS-13, which begins at amino acid 1596 and ends at amino acid 1668 of the amino acid sequence of wild-type human VWF depicted in SEQ ID NO: 1 in the Sequence Listing;

(7) a mutant substrate polypeptide for ADAMTS-13, which has an amino acid sequence homology of at least 50% or higher to the substrate polypeptide for ADAMTS-13 according to any of (1)-to (6) as described above;

(8) a mutant substrate polypeptide for ADAMTS-13, which has an amino acid sequence homology of at least 70% or higher to the substrate polypeptide for ADAMTS-13 according to any of (1) to (6) as described above;

(9) a mutant substrate polypeptide for ADAMTS-13, which has an amino acid sequence homology of at least 90% or higher to the substrate polypeptide for ADAMTS-13 according to any of (1) to (6) as described above;

(10) a mutant substrate polypeptide for ADAMTS-13, which is different from the substrate polypeptide for ADAMTS-13 according to any of (1) to (6) as described above, by one or more amino acid deletion, insertion, substitution, or addition (or combinations thereof) in the amino acid sequence of the substrate polypeptide for ADAMTS-13 according to any of (1) to (6) as described above;

(11) the substrate polypeptide or mutant substrate polypeptide for ADAMTS-13 according to any of (1) to (10) as described above, having a tag sequence attached at the N-terminal and/or at the C-terminal;

(12) the substrate polypeptide or mutant substrate polypeptide for ADAMTS-13 according to (11) as described above, wherein the tag is selected the group consisting of proteins, peptides, coupling agents, radioactive labels, and chromophores;

(13) the substrate polypeptide or mutant substrate polypeptide for ADAMTS-13 according to (11) or (12) as described above, wherein the tag is for immobilization on a solid phase;

(14) the substrate polypeptide or substrate mutant polypeptide for ADAMTS-13 according to (13) as described above, which is immobilized on a solid phase;

(15) a method for measuring ADAMTS-13 activity in a subject, which comprises contacting a substrate polypeptide or mutant substrate polypeptide for ADAMTS-13 according to any of (1) to (14) as described above, with plasma obtained from a normal subject, followed by analyzing resultant polypeptide fragments to make a control; and contacting said substrate polypeptide or mutant substrate polypeptide for ADAMTS-13 according to any of (1) to (14) as described above, with plasma obtained from the subject, followed by analyzing resultant polypeptide fragments in a similar way and making a comparison with the control;

(16) a high throughput method for measuring the activity of ADAMTS-13 in plasma from subjects, which comprises employing a substrate polypeptide or mutant substrate polypeptide for ADAMTS-13 according to any of (1) to (14) as described above;

(17) a diagnostic composition for in vitro test of the decrease or deficiency of ADAMTS-13 activity in a patient, comprising a substrate polypeptide or mutant substrate polypeptide for ADAMTS-13 according to any of (1) to (14) as described above;

(18) a kit for in vitro test of the decrease or deficiency of ADAMTS-13 activity in a patient, comprising as the essential component a substrate polypeptide or mutant substrate polypeptide for ADAMTS-13 according to any of (1) to (14) as described above; and

(19) use of a substrate polypeptide or mutant substrate polypeptide for ADAMTS-13 according to any of (1) to (14) as described above, for producing the diagnostic composition according to (17) as described above or the kit according to (18) as described above.

DETAILED DESCRIPTION OF THE INVENTION

Figure 1:
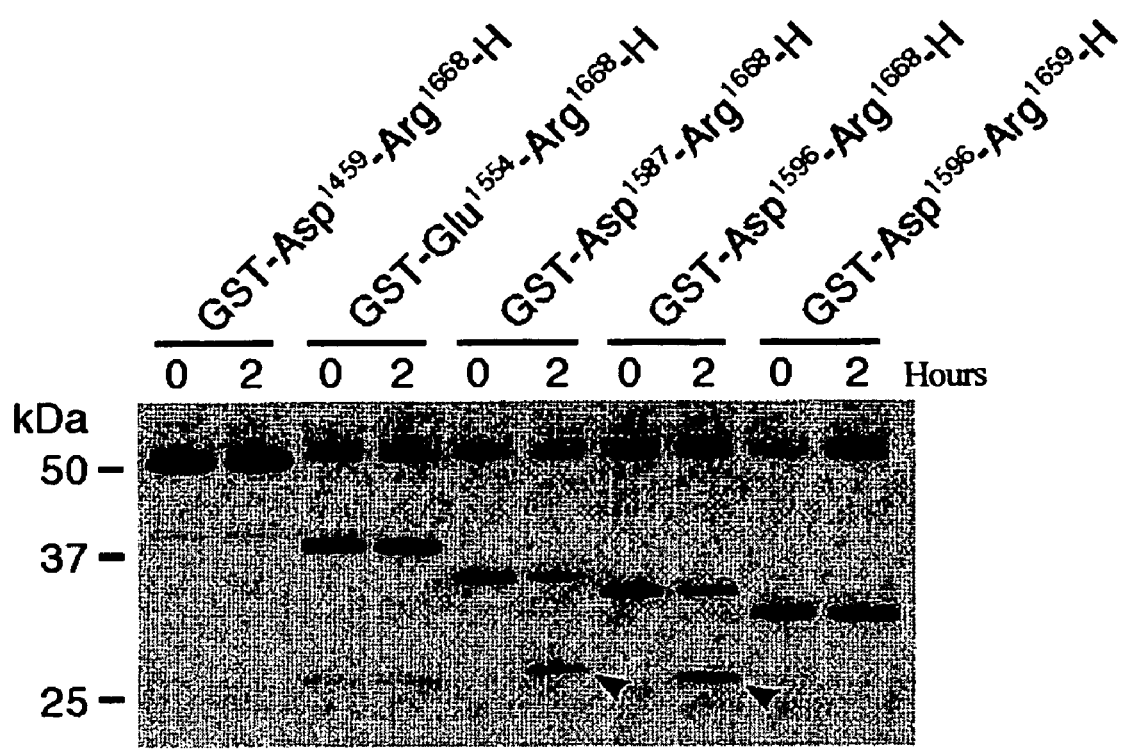
FIG. 1 shows the results of reactions of GST-$Asp^{1459}$-$Arg^{1668}$-H(GST-(SEQ ID NO: 2)-H), GST-$Glu^{1554}$-$Arg^{1668}$-H(GST-(SEQ ID NO: 3)-H), GST-$Asp^{1587}$-$Arg^{1668}$-H(GST-(SEQ ID NO: 4)-H), GST-$Asp^{1596}$-$Arg^{1668}$-H(GST-(SEQ ID NO: 5)-H), and GST-$Asp^{1596}$-$Arg^{1659}$-H(GST-(SEQ ID NO: 6)-H) with normal plasma at 37° C. for 2 hours, followed by separation on SDS-PAGE and western blot employing an anti-GST antibody as the primary antibody.

Wild-type human VWF is a polypeptide composed of 2813 amino acids in all, including its signal peptide and pro region. The amino acid sequence of wild-type human VWF is depicted in SEQ ID NO: 1 in the Sequence Listing. The mature subunit of wild-type human VWF, which is a segment excluding its signal peptide and pro region, is a polypeptide extending from amino acid 764 to amino acid 2813 of SEQ ID NO: 1 in the Sequence Listing. The numbering of the amino acids is as follows: the initial methionine at the amino (N) end of wild-type human VWF is set to be 1 (amino acid 1), and the amino acids are numbered consecutively in the direction toward the carboxyl (C) end (see, SEQ ID NO: 1 in the Sequence Listing). In this specification, the 1459th amino acid from the N-terminal of SEQ ID NO: 1 in the Sequence Listing is sometimes expressed as amino acid 1459, for example. Further, the 1459th amino acid from the N-terminal of SEQ ID NO: 1 in the Sequence Listing is aspartic acid (Asp), and in some cases, is expressed as $Asp^{1459}$. Furthermore, for example, the polypeptide extending from amino acid 1459 (Asp) to amino acid 1668 (Arg) is, in some cases, expressed as $Asp^{1459}$-$Arg^{1668}$.

The amino acid sequence of "wild-type" VWF means the amino acid sequence of human VWF which is not mutated. In this specification, unless specified to be "mutant," amino acid sequences are not intended to be "mutant," even in the absence of the expression of "wild-type."

Therefore, in this specification, if a partial amino acid sequence of the human mature VWF subunit has the same sequence as that of the native human mature VWF subunit corresponding to that segment, the partial sequence is "wild-type," and if a partial amino acid sequence has a different sequence, the partial sequence is "mutant."

As used herein, the VWF is of human origins, unless specified to be from non-human. VWFs originating from non-human organisms are included in "mutant" versions, in this specification.

A "polypeptide" as used herein refers to a peptide having two or more amino acid residues. Further, the terms "polypeptide" and "protein" are used synonymously in this specification.

In this specification, amino acids are expressed by the conventional three-letters.

The present invention, in one embodiment, provides a substrate polypeptide for ADAMTS-13, which begins at one of amino acids 764 to 1605 and ends at one of amino acids 1606 to 2813 of the amino acid sequence of wild-type human VWF depicted in SEQ ID NO: 1 in the Sequence Listing, wherein the polypeptide beginning at amino acid 764 and ending at amino acid 2813 of SEQ ID NO: 1 of the Sequence Listing is excluded.

The substrate polypeptide for ADAMTS-13 according to the present invention has a partial amino acid sequence of the human mature VWF subunit comprising the cleavage site $Tyr^{1605}$-$Met^{1606}$ as the essential component. Therefore, the full-length wild-type human mature VWF subunit is excluded which begins at amino acid 764 and ends at amino acid 2813.

The region from amino acid 1459 (Asp) to amino acid 1668 (Arg) of the amino acid sequence of wild-type human VWF depicted in SEQ ID NO: 1 in the Sequence Listing, which contains no Cys residue, does not cause multimerization due to the formation of disulfide linkage and does not get rise to problems in the specificity for ADAMTS-13, quantitativeness of measuring ADAMTS-13 activity, reproducibility, handling, and others. Therefore, the present invention, in a preferable embodiment, provides a substrate polypeptide for ADAMTS-13, which begins at one of amino acids 1459 to 1605 and ends at one of amino acids 1606 to 1668 of the amino acid sequence of wild-type human VWF depicted in SEQ ID NO: 1 in the Sequence Listing.

Short polypeptides consisting of up to four amino acids in front of and behind the cleavage site, respectively, are not much specific for ADAMTS-13, as a substrate. Therefore, the present invention, in a more preferable embodiment, provides a substrate polypeptide for ADAMTS-13, which begins at one of amino acids 1459 to 1600 and ends at one of amino acids 1611 to 1668 of the amino acid sequence of wild-type human VWF indicated in SEQ ID NO: 1 in the Sequence Listing. The substrate polypeptide for ADAMTS-13 of this embodiment, which contains no Cys residue as mentioned above, does not cause multimerization due to the formation of disulfide linkage and does not get rise to problems in the specificity for ADAMTS-13, quantitativeness of measuring ADAMTS-13 activity, reproducibility, handling, and others. In addition, the polypeptide for ADAMTS-13 of this embodiment is of a small size which is sufficiently suitable for producing it by recombinant methods, and has high specificity for ADAMTS-13.

The present invention, in a further preferable embodiment, provides a substrate polypeptide for ADAMTS-13, which begins at one of amino acids 1554 to 1600 and ends at one of amino acids 1660 to 1668 of the amino acid sequence of wild-type human VWF depicted in SEQ ID NO: 1 in the Sequence Listing. As mentioned above, the substrate polypeptide for ADAMTS-13 of this embodiment, which contains no Cys residue, does not cause multimerization due to the formation of disulfide linkage and does not get rise to problems in the specificity for ADAMTS-13, quantitativeness of measuring ADAMTS-13 activity, reproducibility, handling, and others. The substrate polypeptide for ADAMTS-13 of this embodiment has a smaller size than that of the polypeptide of the above-described embodiment, and thus is particularly suitable for producing-it by recombinant methods. In addition, the substrate polypeptide for ADAMTS-13 of this embodiment has higher specificity for ADAMTS-13 than that of the polypeptide of the above-described embodiment (see, the section of Examples).

The present invention provides, as a particularly preferable specific example, a substrate polypeptide for ADAMTS-13, which begins at amino acid 1587 and ends at amino acid 1668 of the amino acid sequence of wild-type human VWF depicted in SEQ ID NO: 1 in the Sequence Listing, and a substrate polypeptide for ADAMTS-13, which begins at amino acid 1596 and ends at amino acid 1668 of the amino acid sequence of wild-type human VWF depicted in SEQ ID NO: 1 in the Sequence Listing.

These substrate polypeptides for ADAMTS-13 of the present invention are cleaved between $Tyr^{1605}$-$Met^{1606}$ by ADAMTS-13.

In Addition, the present invention, in a further embodiment, provides a mutant substrate polypeptide for ADAMTS-13, which has an amino acid homology of at least 50% or higher, preferably at least 70% or higher, and more preferably at least 90% or higher, to the substrate polypeptide for ADAMTS-13 according to any of the above-described embodiments.

Preferably, the mutant substrate polypeptide for ADAMTS-13 has the cleavage site $Tyr^{1605}$-$Met^{1606}$ contained therein. However, as long as the mutant substrate polypeptide for ADAMTS-13 retains specificity for ADAMTS-13, the two amino acids of the cleavage site may be different from the above-described amino acids ($Tyr^{1605}$, $Met^{1606}$), and such mutant substrate polypeptides for ADAMTS-13 are also encompassed within the present invention.

The "homology" of an amino acid sequence refers to the degree at which two or more amino acid sequences under comparison have the identical or a similar amino acid sequence. For the mutant substrate polypeptides for ADAMTS-13 according to the present invention, amino acid sequences having 100% homology to the wild type are excluded.

Further preferably, a mutant substrate polypeptide for ADAMTS-13 according to the present invention is a mutant substrate polypeptide for ADAMTS-13 which is different from the above-described substrate polypeptide for ADAMTS-13, by one or more amino acid deletion, insertion, substitution, or addition (or combinations thereof) in the amino acid sequence of the above-described substrate polypeptide for ADAMTS-13.

Mutant amino acid sequences can be any sequence, if they are sequences as described, and preferably can be, for example, sequences having one or more amino acid deletion, insertion, substitution, or addition (or combination thereof) in the wild-type amino acid sequence, or sequences having a modified side chain(s) of one or more amino acids of the wild-type amino acid sequence (for example, synthetic, non-naturally occurring amino acids), or combinations of these alterations.

These alterations can result from spontaneous mutation or artificial mutagenesis. Artificial mutagenesis is well known in the art and includes, for example, site-directed mutagenesis employing recombinant procedures, synthesis of mutant polypeptides by chemical processes, such as solid-phase synthesis and liquid-phase synthesis, or chemical modification of amino acid residues, details of each of which are well known to those skilled in the art. Additionally, such mutation and/or modification can be made at any position.

Examples of modifying amino acids are, for example, acetylation, acylation, amidation, addition of sugar chains, addition of nucleotides or nucleotide derivatives, addition of lipids or lipid derivatives, cyclization, formation of disulfide linkage, demethylation, formation of cross-linking, formation of cystine, formation of pyroglutamic acid, formylation, hydroxylation, halogenation, methylation, oxidation of side chains, treatments with proteolytic enzymes, phosphorylation, sulfation, racemization, and others, which are well-known in the art.

Especially when a substrate polypeptide for ADAMTS-13 according-to the present invention is produced in a eukaryotic cell expression system, it is highly likely that a sugar chain is added at a serine or threonine residue(s) of the polypeptide. Substrate polypeptides for ADAMTS-13 which are expressed in this way in eukaryotic cells and undergo the addition of a sugar chain are also included within the present invention.

The following describes methods for producing substrate polypeptides or mutant substrate polypeptides for ADAMTS-13 of the present invention. Although the explanation which follows is made on methods for producing substrate polypeptides for ADAMTS-13 of the present invention, it will be clear to those skilled in the art that the explanation which follows is also applicable to methods for producing mutant substrate polypeptides for ADAMTS-13.

When chemical synthesis is carried out, solid- or liquid-phase peptide synthesis is commonly used. For example, solid-phase peptide synthesizers can be employed. When modification of amino acid residues is required, modified amino acids can be introduced into a synthesizer as appropriate. It is also well known to introduce a protecting group into a sensitive residue during the synthesis. In addition, modifications may be performed after the amino acid sequence is obtained. Needless to say, these and other chemical synthesis procedures are well known in the art, and those skilled-in the art can select an appropriate-procedure to synthesize intended polypeptides.

Alternatively, it is also possible to produce a polypeptide of the present invention by digesting a polypeptide containing the polypeptide of the present invention with an appropriate protease and/or peptidase. For example, a VWF fraction may be separated from plasma and subjected to the reaction with a protease and/or peptidase having a specific cleavage site.

Methods of isolating and purifying resulting polypeptides are also well known in the art, such as chromatography of various types, salting out, electrophoresis, ultrafiltration, and others.

Also, it is possible to produce substrate polypeptides for ADAMTS-13 of the present invention by recombinant procedures. Production of polypeptides by recombinant procedures can be carried out by methods well known to those skilled in the art, such as methods described by Sambrook et al. in Molecular Cloning, 2nd Ed., Cold Spring Harbor Laboratory Press (1989), while typical procedures are described below.

First, DNA coding for a polypeptide of the present invention is cloned. Means for cloning DNA include, for example, methods in which synthetic DNA primers having a partial base sequence of the polypeptide of the present invention are employed so as to allow one to carry out amplification by methods well known in the art, such as PCR procedures. The cloned DNA is ligated into an appropriate expression vector, which in turn is introduced into an appropriate host cell to transform the host cell, and the transformed host cell is cultured, thereby allowing one to obtain the expressed polypeptide. It is preferable that when ligating the cloned DNA into an appropriate expression vector, the DNA is ligated downstream of an appropriate promoter to facilitate its expression for obtaining much amounts of the polypeptide. The nucleotide sequence of human VWF has been deposited on a database, for example, as the GenBank Accession No. NM_000552 and is available.

Expression vectors include plasmids from E. coli (for example, pBR322, pBR325, pUC12, pUC13, and others), plasmids from Bacillus subtilis (for example, pUB10, pTP5, pC194, and others), plasmids from yeast (for example, pSH19, pSH15, and others), bacteriophages (for example, lambda phage and others), baculoviruses, animal viruses (for example, retrovirus, vaccinia virus, and others), or pA1-11, pXXT1, pRc, pcDNAI, and the like. These and other vectors are well known to those skilled in the art, and many vectors are commercially available (for example, pGEX-6P-1, which is commercially available from Amersham-Bioscience, is a vector allowing for expression of fusion proteins with a tag protein, glutathione-S-transferase).

Host cells include bacterial cells, such as E. coli (for example, strains K12, HB101, JM103, JA221, C600, BL21, and others), Bacillus subtilis, and genera Streptococcus, Staphylococcus, Enterococcus; fungus cells, such as yeast cells and Asperguillus cells; insect cells, such as Drosophila S2 and Spodoptera Sf9 cells; animal cells, such as CHO, COS, HeLa, C127, 3T3, BHK, 293 cells; and plant cells.

Any promoters can be used, as long as they are suitable for host cells which are employed for the expression of DNA coding an intended polypeptide; for E. coli hosts, trp, lac, recA promoters, for example, are employed; for Bacillus subtilis hosts, SPO1, SPO2, penP promoters, for example; for yeast hosts, PHO5 and PGK promoters, for example; for insect hosts, P10 and polyhedron promoters, for example; for animal cell hosts, SV40 early, SR-alpha, CMV promoters, for example.

Expression vectors may further contain, if desired, enhancers, splicing signals, poly A addition signals, selectable markers (antibiotic-resistance genes such as genes resistant to methotrexate, ampicillin, and neomycin, dihydrofolate reductase gene, and others).

Transformation of host cells can be performed according to methods described in many texts, including the above-described text by Sambrook et al., such as calcium phosphate protocols, methods employing DEAE-dextran, microinjection, electroporation, and virus infection.

When culturing the transformants, liquid media are suitable as a medium which can be used, and preferable medium compositions and culture conditions for respective host types are well known in the art, and can be selected by those skilled in the art.

It is possible to incorporate an appropriate secretion signal into a polypeptide to be expressed, in order to allow the translated polypeptide to be secreted into the endoplasmic reticulum lumen, periplasmic space, or extracellular environment. Such a signal may be a signal native or heterologous to the polypeptide.

Expressed recombinant polypeptides can be recovered and purified from recombinant cell cultures by well-known methods, including, for example, ammonium sulfate or ethanol precipitation, precipitation with organic solvents, electrophoresis, ultrafiltration, anion- or cation-exchange chromatography, phosphocellulose chromatography, hydrophobic interaction chromatography, affinity chromatography, hydroxylapatite chromatography, and lectin chromatography, and others. It is preferable to employ high performance liquid chromatography for purification. In the case where the polypeptide is denatured during the isolation and/or purification, for example, where the polypeptide is produced as inclusion body within the bacterial cell, well-known techniques for the regeneration of polypeptides, such as urea treatment, can be utilized to make the denatured polypeptide have the active conformation again.

The following describes the determination of the activity using a substrate polypeptide or mutant polypeptide for ADAMTS-13 of the present invention, and diagnostic compositions and kits comprising such a polypeptide. Although the explanation which follows is made with respect to substrate polypeptides for ADAMTS-13, it will be clear to those skilled in the art that the explanation which follows is also applicable to mutant polypeptides for ADAMTS-13.

The activity of ADAMTS-13 in a subject can be measured using a substrate polypeptide for ADAMTS-13 of the present invention, for example, in the following procedures: Under appropriate reaction conditions, a substrate polypeptide for ADAMTS-13 of the present invention is contacted with plasma obtained from a normal subject, and resultant polypeptide fragments are analyzed, for example, on SDS-polyacrylamide gel (hereinafter, referred to as "SDS-PAGE") to make a control, and the substrate polypeptide for ADAMTS-13 of the present invention is contacted with plasma obtained from a subject and subjected to SDS-PAGE in a similar way, followed by staining of proteins by Coomassie Blue or silver staining or the like and analyzing the products to compare the band position, density, and the like with the control. Alternatively, it may be possible to carry out western blotting following the SDS-PAGE. The reaction solution preferably contains divalent metal ions, such as $Ba^{2+}$, which are an ADAMTS-13 activator, and in addition, a buffer solution whose pH corresponds to the optimal pH of 8 to 9 of ADAMTS-13.

Thus, the present invention relates to a method for measuring the activity of ADAMTS-13 in a subject plasma, which comprises contacting a substrate polypeptide for ADAMTS-13 of the present invention with plasma obtained from a subject and analyzing the product, as described above.

The present invention also relates to a diagnostic composition for in vitro test of the decrease or deficiency of ADAMTS-13 activity in a subject, and therefore the presence of TTP or the predisposition to TTP, or for making a definitive diagnosis of TTP and a discrimination between TTP and HUS, wherein the composition comprises a substrate polypeptide for ADAMTS-13 of the present invention. The present invention further relates to a kit for in vitro test of the decrease or deficiency of ADAMTS-13 activity in a subject, and therefore the presence of TTP or the predisposition to TTP, or for making a definitive diagnosis of TTP and a discrimination between TTP and HUS, wherein the kit comprises as the essential component a substrate polypeptide for ADAMTS-13 of the present invention. The kit usually has its instructions accompanied therewith.

A substrate polypeptide or mutant polypeptide for ADAMTS-13 of the present invention may have a tag sequence attached at the N-terminal and/or at the C-terminal. Although the explanation which follows is made with respect to substrate polypeptides for ADAMTS-13, it will be clear to those skilled in the art that a tag also can be attached to mutant polypeptides for ADAMTS-13 and used in a similar way. The tag sequence may be any one, and preference is given to tag sequences which facilitate, for example, detection, quantification, and separation of cleaved products by ADAMTS-13. Also, the tag sequence may be for immobilizing a substrate polypeptide for ADAMTS-13 of the present invention onto a solid phase. The present invention also encompasses substrate polypeptides for ADAMTS-13 which are immobilized onto a solid phase using such tag sequences. The tag sequences include proteins (for example, glutathione transferase (hereinafter, referred to as "GST"), luciferase, beta-galactosidase, and others), peptides (for example, His tag and others), coupling agents (carbodiimide reagents and others), various kinds of labels (for example, radioactive labels, chromophores, enzymes, and others), and those skilled in the art can select the type of tags according to the purpose. Methods for attaching of tag are well known to those skilled in the art.

For example, as detailed in Example 1, DNA coding for a substrate polypeptide for ADAMTS-13 of the present invention may be inserted into the *E. coli* expression vector pGEX-6P-1 to obtain a fusion protein having, as a tag, GST fused at the N-terminal of the substrate polypeptide for ADAMTS-13 of the present invention. In this case, the fusion protein can be purified by affinity chromatography employing a glutathione sepharose column. For example, when macromolecules such as GST protein are fused, two fragments whose molecular weights are significantly different can be analyzed after the reaction; for example, the reaction products are separated, for example, on SDS-PAGE, whereby their analysis will become easier. In this case, when an anti-GST antibody is available, the antibody can be used for western blotting.

In addition, for example, luciferase or galactosidase as a tag sequence may be fused at the C-terminal of a substrate polypeptide for ADAMTS-13 of the present invention and GST at the N-terminal. In this case, the fusion protein can be trapped, for example, on glutathione beads, and the tagged product which is released after the cleavage with ADAMTS-13 can be quantified by well known methods for measuring the activity of luciferase or galactosidase, thereby determining the ADAMTS-13 activity.

Further, well-known His tags, anti-Myc tags, and others can be also used as tag sequences. For example, a His tag is added at the N-terminal of a substrate polypeptide for ADAMTS-13 of the present invention for immobilization onto a solid phase and a horseradish peroxides (HRP) labeled anti-Myc tag at the C-terminal. After the reaction with ADAMTS-13, the HRP released into the liquid phase can be determined colorimeterically by well-known methods, thereby determining the ADAMTS-13 activity.

In addition, a specific embodiment as described below is also considered to be an embodiment in which a tag is added to a substrate polypeptide for ADAMTS-13 of the present invention. Accordingly, a known protein is selected whose activity-measuring method has been already established, and the amino acid sequence of a substrate polypeptide for ADAMTS-13 of the present invention is inserted into the amino acid sequence of the known protein so as to retain the activity of the known protein, thereby to obtain a fusion protein. This fusion protein has been adapted such that when the fusion protein is reacted with plasma obtained from a subject and cleaved at the cleavage site by the ADAMTS-13 activity in plasma, the activity of the initial known protein becomes lost. This type of fusion protein also can be used to determine the activity of ADAMTS-13 in plasma by measuring the degree of the loss of the activity of the fusion protein.

It is also possible to make a substrate polypeptide or mutant substrate polypeptide for ADAMTS-13 of the present invention suitable for high throughput measuring of ADAMTS-13 activity, for example, by addition of a tag allowing or facilitating detection, or by immobilization onto a solid phase. Therefore, the present invention relates to a method, preferably a high throughput method, for measuring the activity of ADAMTS-13 in plasma from subjects, wherein the method is characterized by employing preferably a substrate polypeptide or mutant substrate polypeptide for ADAMTS-13 of the present invention to which a tag is added. The present invention also relates to a composition or a kit for measuring the activity of ADAMTS-13 in plasma, wherein the composition or the kit comprises a substrate polypeptide or mutant substrate polypeptide for ADAMTS-13 of the present invention to which a tag is added.

In further embodiments, the present invention relates to use of a substrate polypeptide or mutant substrate polypeptide for ADAMTS-13 as described above, for producing the diagnostic composition or the kit as described above.

EXAMPLES

A. Production of Substrate Peptides for ADAMTS-13

As mentioned above, ADAMTS-13 specifically cleaves the peptide bond between $Tyr^{1605}$-$Met^{1606}$ of VWF. In fact, however, VWF undergoes the aggregation of many mature subunits, resulting in the formation of huge molecules, and thus causes problems in the quantitativeness, reproducibility, operationality, and the like, when as in conventional measuring methods, native VWF is used as the substrate. In the present invention, measuring of the enzymatic activity of ADAMTS-13 utilizes, as the substrate, partial sequences of the mature VWF subunit which contain sequences around its cleavage site, thereby leading to the solution of these problems.

The partial sequences should in general have a certain length in order to retain the substrate specificity for ADAMTS-13, whereas it would be better that they have a small size in order to make them suitable for production through recombinant expression by $E.\ coli$. When used as the substrate, the partial sequences should represent regions containing no cysteine residue, since the presence of a cysteine residue having an SH group in a polypeptide may cause multimerization, resulting in problems in the quantitativeness, handling, reproducibility, and the like. We selected the polypeptide $Asp^{1459}$-$Arg^{1668}$ as a polypeptide meeting these requirements. That is, this region is the longest segment that contains the cleavage site and carries no cysteine residue.

RT-PCR was carried out using, as the template, RNA extracted from commercially available human umbilical vein endothelial cells, to obtain cDNA coding for the $Asp^{1459}$-$Arg^{1668}$ region of the VWF subunit (SEQ ID NO: 2). The sense-direction primer used was 5'-cgggatccGACCTTGC-CCCTGAAGCCCCTC-3' (SEQ ID NO: 7) and the antisense-direction primer was 5'-ggaattcTCAGTGATGGTGATGGT-GATGCCTCTGCAGCACCAGGTCAGGA-3' (SEQ ID NO: 8) (the portions of lower case letters represent restriction enzyme recognition sites added for subcloning). The antisense-direction primer has a 6×His tag sequence added thereto. The PCR product was digested with BamHI and EcoRI and then inserted into the $E.\ coli$ expression vector pGEX-6P-1 (Amersham-Bioscience) which had been digested with the same enzymes, BamHI and EcoRI, so as to express a fusion protein which has glutathione-S-transferase (GST) attached at the N-terminal and the 6×His tag sequence attached at the C-terminal of the $Asp^{1459}$-$Arg^{1668}$ region of the VWF subunit (hereinafter, designated as GST-$Asp^{1459}$-$Arg^{1668}$-H(GST-(SEQ ID NO: 2)-H)). The resulting expression vector was introduced into $E.\ coli$ strain BL21, which in turn was subjected to transient expression by IPTG induction, followed by purification through nickel-affinity chromatography and glutathione-affinity chromatography to obtain the fusion protein GST-$Asp^{1459}$-$Arg^{1668}$-H(GST-(SEQ ID NO: 2)-H.

Smaller polypeptides than the above-described polypeptide are more suitable for production by recombinant methods using $E.\ coli$ or others. In order to obtain cDNAs coding the $Glu^{1554}$-$Arg^{1668}$ (SEQ ID NO: 3) $Asp^{1587}$-$Arg^{1668}$ (SEQ ID NO: 4) $Asp^{1596}$-$Arg^{1668}$ (SEQ ID NO: 5), and $Asp^{1596}$-$Arg^{1659}$ (SEQ ID NO: 6) regions, three sense-direction primers 5'-cgggatccGAGGCACAGTCCAAAGGGGACA-3' (SEQ ID NO: 9), 5'-cgggatccGACCACAGCTTCTTGGT-CAGCC-3' (SEQ ID NO: 10), and 5'-cgggatccGACCGG-GAGCAGGCGCCCAACC-3' (SEQ ID NO: 11), and one antisense-direction primer 5'-cggaattcTCAGTGATGGT-GATGGTGATGTCGGGGGAGCGTCTCAAAGTCC-3' (SEQ ID No: 12) were employed. They were combined and processed in a similar way to produce plasmids allowing the expression of four fusion proteins, GST-$Glu^{1554}$-$Arg^{1668}$-H (GST-(SEQ ID NO: 3)-H), GST-$Asp^{1587}$-$Arg^{1668}$-H(GST-(SEQ ID NO: 4)-H), GST-$Asp^{1596}$-$Arg^{1668}$-H(GST-(SEQ ID NO: 5)-H), and GST-$Asp^{1596}$-$Arg^{1659}$-H(GST-(SEQ ID NO: 6)-H). Each of these expression vectors was introduced into $E.\ coli$ strain BL21, which in turn was subjected to transient expression by IPTG induction, followed by purification through nickel-affinity chromatography and glutathione-affinity chromatography to obtain each of the fusion proteins.

When the five fusion proteins thus produced, GST-$Asp^{1459}$-$Arg^{1668}$-H(GST-(SEQ ID NO: 2)-H), GST-$Glu^{1554}$-$Arg^{1668}$-H(GST-(SEQ ID NO: 3-H(GST-$Asp^{1587}$-$Arg^{1668}$-H (GST-SEQ ID NO: 4)-H), GST-$Asp^{1596}$-$Arg^{1668}$-H(GST-(SEQ ID NO: 5)-H), and GST-$Asp^{1596}$-$Arg^{1659}$-H(GST-(SEQ ID NO: 6)-H), are specifically cleaved by ADAMTS-13, that is, when the site corresponding to the site between $Tyr^{1605}$-$Met^{1606}$ of the VWF subunit is cleaved, these fusion proteins will be separated into two fragments of 43.1 kDa (including the GST portion) and 7.7 kDa (including the His6 tag sequence portion), of 32.7 kDa and 7.7 kDa, of 29.0 kDa and 7.7 kDa, of 28.0 kDa and 7.7 kDa, and of 28.0 kDa and 6.7 kDa, respectively.

B. Reaction of Substrate Polypeptides for ADAMTS-13 with Plasma ADAMTS-13

These fusion proteins were subjected to reactions with 0.25 μL of normal plasma at 37° C. for zero and two hours. The total reaction volume was 20 μL, containing 25 mM Tris (pH 8.0), 10 mM $BaCl_2$, 4 mM glutathione, 1 mM APMSF. The reaction solutions were subjected to SDS-polyacrylamide gel electrophoresis for separation of the product, followed by western blotting using an anti-GST antibody as the primary antibody. The results are shown in FIG. 1.

In the case of the two-hour reaction, the expected fragment (indicated by the arrowheads in the figure) was clearly yielded for GST-$Asp^{1587}$-$Arg^{1668}$-H(GST-(SEQ ID NO: 4)-H) and GST $Asp^{1596}$-$Arg^{1668}$-H(GST-(SEQ ID NO: 5)-H), while a very faint band was produced at the expected position, also for GST-$Glu^{1554}$-$Arg^{1668}$-H(GST-(SEQ ID NO: 3)-H) having a longer region. It proved that GST-$Asp^{1459}$-$Arg^{1668}$-H(GST-(SEQ ID NO: 2)-H) having a further longer region and GST-$Asp^{1596}$-$Arg^{1659}$-H(GST-(SEQ ID NO: 6)-H) having a shorter region did not give the fragment or was difficult to give the fragment. These results suggested that GST- Asp$^{1587}$-Arg$^{1668}$-H(GST-(SEQ ID NO: 4)-H) and GST-Asp$^{1596}$-Arg$^{1668}$-H(GST-(SEQ ID NO: 5)-H) be suitable as a substrate for ADAMTS-13.

C. Substrate Specificity and Reaction Quantitativeness of Substrate Polypeptides for ADAMTS-13

Figure 2:
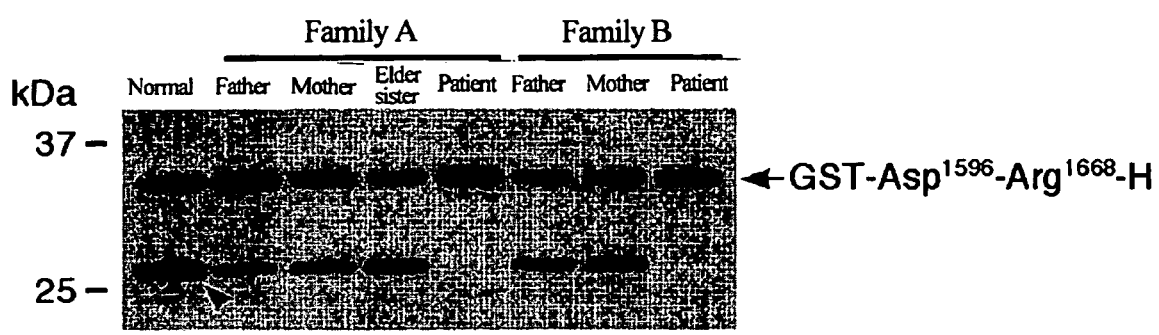
FIG. 2 shows the substrate specificity and reaction quantitativeness of GST-$Asp^{1596}$-$Arg^{1668}$-H (GST-(SEQ ID NO: 5)-H). The reaction conditions were the same as in FIG. 1.

In order to examine the specificity of GST-Asp$^{1596}$-Arg$^{1668}$-H (GST-(SEQ ID NO: 5)-H) as the substrate, among the particularly preferable substrate polypeptides for ADAMTS-13 obtained in Section B, it was reacted with plasma samples from TTP-patient family members. The reaction conditions and detection method were the same as described above. The results are shown in FIG. 2.

When each of plasma samples from two patients was reacted with GST-Asp$^{1596}$-Arg$^{1668}$-H(GST-(SEQ ID NO: 5)-H), there was not detected the fragment which is yielded by the reaction with normal plasma (indicated by the arrowhead in the figure). On the other hand, for plasma samples from mother and elder sister of family A, and from father and mother of family B which were found to have about one-half of the activity of ADAMTS-13 in normal plasma by another method, the fragment was yielded at smaller amounts than with the normal plasma. For a plasma sample from father of family A which was found to have an even lower activity, the fragment was yielded only at a further reduced amount. These results suggest that GST-Asp$^{1596}$-Arg$^{1668}$-H(GST-(SEQ ID NO: 5)-H) is a specific artificial substrate which is cleaved quantitatively by ADAMTS-13 in plasma and is not cleaved by other enzymes.

INDUSTRIAL APPLICABILITY

The substrates polypeptides for measuring ADAMTS-13 activity of the present invention are small polypeptides which retain the substrate specificity and at the same time, are suitable for their production by recombinant expression by *E. coli*. In addition, the polypeptides contain no cysteine residue having a SH group, and thus can avoid the problem of their multimerization and also get rise to few problems relating to the quantitativeness, handling, reproducibility, and others. Therefore, the substrates polypeptides for measuring ADAMTS-13 activity of the present invention are capable of performing simple, specific, quantitative, reproducible, and sensitive measurement of ADAMTS-13 activity. The substrates polypeptides for measuring ADAMTS-13 activity of the present invention are also suitable for multi-sample processing. For example, multi-sample processing can be carried out, for example, by immobilizing or labeling a substrate polypeptide for measuring ADAMTS-13 activity of the present invention.

The present invention enables one to make an effective treatment of TTP and a prediction of the onset of TTP. Specifically, the present invention allow one to obtain clinical information that the activity is not decreased, that is, no sign of developing TTP appears, by periodically measuring the activity of ADAMTS-13 in the blood, for example, during taking drugs that have side effects of developing TTP, and during the pregnancy tending to induce TTP. In addition, the present invention provides as a powerful tool for revealing the relationship between the ADAMTS-13 activity and a variety of diseases by epidemiological research. The present invention also allows one to make a rapid, definitive diagnosis of patients suffering from TTP. Further, the present invention allows one to make a precise measurement of the ADAMTS-13 activity of patients, thereby making a discrimination between TTP and HUS.

Free Text in the Sequence Listing

SEQ ID NO: 1 depicts the amino acid sequence of wild-type human VWF.

SEQ ID NO: 2 depicts the amino acid sequence of Asp$^{1459}$-Arg$^{1668}$, a substrate polypeptide for ADAMTS-13 of the present invention.

SEQ ID NO: 3 depicts the amino acid sequence of Glu$^{1554}$-Arg$^{1668}$, a substrate polypeptide for ADAMTS-13 of the present invention.

SEQ ID NO: 4 depicts the amino acid sequence of Asp$^{1587}$-Arg$^{1668}$, a substrate polypeptide for ADAMTS-13 of the present invention SEQ ID NO: 5 depicts the amino acid sequence of Asp$^{1596}$-Arg$^{1668}$, a substrate polypeptide for ADAMTS-13 of the present invention.

SEQ ID NO: 6 depicts the amino acid sequence of Asp$^{1596}$-Arg$^{1659}$, a substrate polypeptide for ADAMTS-13 of the present invention.

SEQ ID NO: 7 depicts the nucleotide sequence of the sense primer used for producing Asp$^{1459}$-Arg$^{1668}$ (SEQ ID NO: 2) a substrate polypeptide for ADAMTS-13 of the present invention.

SEQ ID NO: 8 depicts the nucleotide sequence of the anti-sense primer used for producing Asp$^{1459}$-Arg$^{1668}$ (SEQ ID NO: 2), a substrate polypeptide for ADAMTS-13 of the present invention.

SEQ ID NO: 9 depicts the nucleotide sequence of the sense primer used for producing Glu$^{1554}$-Arg$^{1668}$ (SEQ ID NO: 3), Asp$^{1587}$-Arg$^{1668}$ (SEQ ID NO: 4), Asp$^{1596}$-Arg$^{1668}$ (SEQ ID NO: 5), and Asp$^{1596}$-Arg$^{1659}$ (SEQ ID NO: 6), substrate polypeptides for ADAMTS-13 of the present invention.

SEQ ID NO: 10 depicts the nucleotide sequence of the sense primer used for producing Glu$^{1554}$-Arg$^{1668}$ (SEQ ID NO: 3), Asp$^{1587}$-Arg$^{1668}$ (SEQ ID NO: 4), Asp$^{1596}$-Arg$^{1668}$ (SEQ ID NO: 5), and Asp$^{1596}$-Arg$^{1659}$ (SEQ ID NO: 6), substrate polypeptides for ADAMTS-13 of the present invention.

SEQ ID NO: 11 depicts the nucleotide sequence of the sense primer used for producing Glu$^{1554}$-Arg$^{1668}$ (SEQ ID NO: 3), Asp$^{1587}$-Arg$^{1668}$ (SEQ ID NO: 4), Asp$^{1596}$-Arg$^{1668}$ (SEQ ID NO: 5), and Asp$^{1596}$-Arg$^{1659}$ (SEQ ID NO: 6), substrate polypeptides for ADAMTS-13 of the present invention.

SEQ ID NO: 12 indicates the nucleotide sequence of the anti-sense primer used for producing Glu$^{1554}$-Arg$^{1668}$ (SEQ ID NO: 3), Asp$^{1587}$-Arg$^{1668}$ (SEQ ID NO: 4), Asp$^{1596}$-Arg$^{1668}$ (SEQ ID NO: 5), and Asp$^{1596}$-Arg$^{1659}$ (SEQ ID NO: 6), substrate polypeptides for ADAMTS-13 of the present invention.

REFERENCES

1) Levy G G et al., Nature, 2001, 413:488-494.
2) Dent J A et al., Proc Natl Acad Sci USA, 1990, 87:6306-6310.
3) Furlan M et al., Blood, 1996, 87:4223-4234.
4) Gerritsen H et al., Thromb Haemost, 1999, 82:1386-1389.
5) Obert B et al., Thromb Haemost, 1999, 82:1382-1385.
6) Furlan M et al., Seminars in Thromb and Hemost, 2002, 28(2):167-171.

The invention claimed is:

1. An isolated substrate polypeptide for a disintegrin-like and metalloprotease with thrombospondin type-1 motif, 13 (ADAMTS-13), and an optionally included covalently attached heterologous tag, wherein the isolated substrate polypeptide consists of amino acids 1587 to 1668 of the amino acid sequence of wild-type human von Willebrand factor (VWF) in SEQ ID NO: 1, wherein the tag is attached at the N-terminal and/or at the C-terminal of said polypeptide and said tag is selected from the group consisting of a glutathione transferase (GST) luciferase, beta-galactosidase, His tag peptides, coupling agents, radioactive labels, and chromophores.

2. An isolated substrate polypeptide for a disintegrin-like and metalloprotease with thrombospondin type-1 motif, 13 (ADAMTS-13), and an optionally included covalently attached heterologous tag, wherein the isolated substrate polypeptide consists of amino acids 1596 to 1668 of the amino acid sequence of wild-type human von Willebrand factor (VWF) in SEQ ID NO: 1, wherein the tag is attached at the N-terminal and/or at the C-terminal of said polypeptide and said tag is selected from the group consisting of a glutathione transferase (GST) luciferase, beta-galactosidase, His tag peptides, coupling agents, radioactive labels, and chromophores.

3. An isolated polypeptide consisting of an amino acid sequence identity of at least 90% or higher to a) a polypeptide consisting of amino acids 1587 to 1668 of SEQ ID NO: 1, or b) a polypeptide consisting of amino acids 1596 to 1668 of SEQ ID NO: 1, wherein said isolated polypeptide has 1605th Tyr and 1606th Met of SEQ ID NO: 1, and the 1605th Tyr and 1606th Met of SEQ ID NO: 1 is a cleavage site for ADAMTS-13, wherein the isolated polypeptide is cleaved by ADAMTS-13.

4. A polypeptide consisting of the isolated polypeptide of claim 3 and a covalently attached heterologous tag at the N-terminal and/or at the C-terminal of the isolated polypeptide of claim 3, wherein said tag is selected from the group consisting of glutathione transferase (GST), luciferase, beta-galactosidase, His tag peptides, coupling agents, radioactive labels, and chromophores.

5. The polypeptide according to claim 4, wherein the tag is for immobilization on a solid phase.

6. A kit for in vitro testing of a decrease or deficiency of ADAMTS-13 protease activity in a patient, consisting essentially of the polypeptide according to claim 5.

7. The polypeptide according to claim 5, which is immobilized on a solid phase.

8. A kit for in vitro testing of a decrease or deficiency of ADAMTS-13 protease activity in a patient, consisting essentially of the polypeptide according to claim 7.

9. A kit for in vitro testing of a decrease or deficiency of ADAMTS-13 protease activity in a patient, consisting essentially of the polypeptide according to claim 4.

10. A kit for in vitro testing of a decrease or deficiency of ADAMTS-13 protease activity in a patient, consisting essentially of the polypeptide according to claim 3.

11. The polypeptide according to claim 3, wherein said polypeptide contains no Cys residue.

12. A diagnostic composition for in vitro testing of a decrease or deficiency of ADAMTS-13 protease activity in a patient, comprising the substrate polypeptide for ADAMTS-13 according to claim 1 or 2, or the polypeptide according to claim 3.

13. A kit for in vitro testing of a decrease or deficiency of ADAMTS-13 protease activity in a patient, consisting essentially of the substrate polypeptide for ADAMTS-13 according to claim 1 or 2.

14. The substrate polypeptide for ADAMTS-13 according to claim 1 or 2, wherein said tag is for immobilization on a solid phase.

15. The substrate polypeptide for ADAMTS-13, according to claim 14, which is immobilized on a solid phase.

16. A kit for in vitro testing of a decrease or deficiency of ADAMTS-13 protease activity in a patient, consisting essentially of component the substrate polypeptide for ADAMTS-13 according to claim 15.

17. A kit for in vitro testing of a decrease or deficiency of ADAMTS-13 protease activity in a patient, consisting essentially of the substrate polypeptide for ADAMTS-13 according to claim 14.

18. A method for measuring ADAMTS-13 protease activity in a test subject, which comprises:
    (a) contacting the polypeptide according to claim 3 with plasma obtained from a normal subject, and analyzing fragmentation of the polypeptide according to claim 3 to make a control; and
    (b) contacting the polypeptide according to claim 3 with plasma obtained from the test subject, analyzing fragmentation of the polypeptide according to claim 3 and making a comparison with the control, thereby determining ADAMTS-13 protease activity.

19. A high throughput method for measuring ADAMTS-13 protease activity in plasma from subjects, which comprises:
    (a) contacting the polypeptide according to claim 3 with plasma obtained from said subjects; and
    (b) analyzing fragmentation(s) of the polypeptide according to claim 3.

* * * * *

SEQUENCE LISTING

<160> NUMBER OF SEQ ID NOS: 12

<210> SEQ ID NO 1
<211> LENGTH: 2813
<212> TYPE: PRT
<213> ORGANISM: Homo sapiens

<400> SEQUENCE: 1

```
Met Ile Pro Ala Arg Phe Ala Gly Val Leu Ala Leu Ala Leu Ile
 1               5                  10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
             35                  40                  45

Ser Met Tyr Ser Phe Ala Gly Tyr Cys Ser Tyr Leu Leu Ala Gly Gly
         50                  55                  60

Cys Gln Lys Arg Ser Phe Ser Ile Ile Gly Asp Phe Gln Asn Gly Lys
 65                  70                  75                  80

Arg Val Ser Leu Ser Val Tyr Leu Gly Glu Phe Phe Asp Ile His Leu
                 85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
    195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
    275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
```

-continued

```
                355                 360                 365
Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
        450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
        530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
        610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
        690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
        770                 775                 780
```

```
Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
                835                 840                 845

Cys Val Cys Arg Asp Arg Lys Trp Asn Cys Thr Asp His Val Cys Asp
                850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Lys Arg Val Thr Ile Leu
                915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp Gly Ile Gln Asn Asn Asp Leu Thr
                995                 1000                1005

Ser Ser Asn Leu Gln Val Glu Glu Asp Pro Val Asp Phe Gly Asn Ser
        1010                1015                1020

Trp Lys Val Ser Ser Gln Cys Ala Asp Thr Arg Lys Val Pro Leu Asp
1025                1030                1035                1040

Ser Ser Pro Ala Thr Cys His Asn Asn Ile Met Lys Gln Thr Met Val
                1045                1050                1055

Asp Ser Ser Cys Arg Ile Leu Thr Ser Asp Val Phe Gln Asp Cys Asn
                1060                1065                1070

Lys Leu Val Asp Pro Glu Pro Tyr Leu Asp Val Cys Ile Tyr Asp Thr
                1075                1080                1085

Cys Ser Cys Glu Ser Ile Gly Asp Cys Ala Cys Phe Cys Asp Thr Ile
                1090                1095                1100

Ala Ala Tyr Ala His Val Cys Ala Gln His Gly Lys Val Val Thr Trp
1105                1110                1115                1120

Arg Thr Ala Thr Leu Cys Pro Gln Ser Cys Glu Glu Arg Asn Leu Arg
                1125                1130                1135

Glu Asn Gly Tyr Glu Cys Glu Trp Arg Tyr Asn Ser Cys Ala Pro Ala
                1140                1145                1150

Cys Gln Val Thr Cys Gln His Pro Glu Pro Leu Ala Cys Pro Val Gln
                1155                1160                1165

Cys Val Glu Gly Cys His Ala His Cys Pro Pro Gly Lys Ile Leu Asp
        1170                1175                1180

Glu Leu Leu Gln Thr Cys Val Asp Pro Glu Asp Cys Pro Val Cys Glu
1185                1190                1195                1200
```

-continued

```
Val Ala Gly Arg Arg Phe Ala Ser Gly Lys Lys Val Thr Leu Asn Pro
                1205                1210                1215

Ser Asp Pro Glu His Cys Gln Ile Cys His Cys Asp Val Val Asn Leu
            1220                1225                1230

Thr Cys Glu Ala Cys Gln Glu Pro Gly Gly Leu Val Val Pro Pro Thr
        1235                1240                1245

Asp Ala Pro Val Ser Pro Thr Thr Leu Tyr Val Glu Asp Ile Ser Glu
    1250                1255                1260

Pro Pro Leu His Asp Phe Tyr Cys Ser Arg Leu Leu Asp Leu Val Phe
1265                1270                1275                1280

Leu Leu Asp Gly Ser Ser Arg Leu Ser Glu Ala Glu Phe Glu Val Leu
            1285                1290                1295

Lys Ala Phe Val Val Asp Met Met Glu Arg Leu Arg Ile Ser Gln Lys
        1300                1305                1310

Trp Val Arg Val Ala Val Val Glu Tyr His Asp Gly Ser His Ala Tyr
    1315                1320                1325

Ile Gly Leu Lys Asp Arg Lys Arg Pro Ser Glu Leu Arg Arg Ile Ala
    1330                1335                1340

Ser Gln Val Lys Tyr Ala Gly Ser Gln Val Ala Ser Thr Ser Glu Val
1345                1350                1355                1360

Leu Lys Tyr Thr Leu Phe Gln Ile Phe Ser Lys Ile Asp Arg Pro Glu
            1365                1370                1375

Ala Ser Arg Ile Ala Leu Leu Leu Met Ala Ser Gln Glu Pro Gln Arg
        1380                1385                1390

Met Ser Arg Asn Phe Val Arg Tyr Val Gln Gly Leu Lys Lys Lys Lys
        1395                1400                1405

Val Ile Val Ile Pro Val Gly Ile Gly Pro His Ala Asn Leu Lys Gln
    1410                1415                1420

Ile Arg Leu Ile Glu Lys Gln Ala Pro Glu Asn Lys Ala Phe Val Leu
1425                1430                1435                1440

Ser Ser Val Asp Glu Leu Glu Gln Gln Arg Asp Glu Ile Val Ser Tyr
            1445                1450                1455

Leu Cys Asp Leu Ala Pro Glu Ala Pro Pro Pro Thr Leu Pro Pro His
        1460                1465                1470

Met Ala Gln Val Thr Val Gly Pro Gly Leu Leu Gly Val Ser Thr Leu
    1475                1480                1485

Gly Pro Lys Arg Asn Ser Met Val Leu Asp Val Ala Phe Val Leu Glu
    1490                1495                1500

Gly Ser Asp Lys Ile Gly Glu Ala Asp Phe Asn Arg Ser Lys Glu Phe
1505                1510                1515                1520

Met Glu Glu Val Ile Gln Arg Met Asp Val Gly Gln Asp Ser Ile His
            1525                1530                1535

Val Thr Val Leu Gln Tyr Ser Tyr Met Val Thr Val Glu Tyr Pro Phe
        1540                1545                1550

Ser Glu Ala Gln Ser Lys Gly Asp Ile Leu Gln Arg Val Arg Glu Ile
    1555                1560                1565

Arg Tyr Gln Gly Gly Asn Arg Thr Asn Thr Gly Leu Ala Leu Arg Tyr
    1570                1575                1580

Leu Ser Asp His Ser Phe Leu Val Ser Gln Gly Asp Arg Glu Gln Ala
1585                1590                1595                1600

Pro Asn Leu Val Tyr Met Val Thr Gly Asn Pro Ala Ser Asp Glu Ile
            1605                1610                1615

Lys Arg Leu Pro Gly Asp Ile Gln Val Val Pro Ile Gly Val Gly Pro
```

-continued

```
                1620                1625                1630
Asn Ala Asn Val Gln Glu Leu Glu Arg Ile Gly Trp Pro Asn Ala Pro
        1635                1640                1645
Ile Leu Ile Gln Asp Phe Glu Thr Leu Pro Arg Glu Ala Pro Asp Leu
    1650                1655                1660
Val Leu Gln Arg Cys Cys Ser Gly Glu Gly Leu Gln Ile Pro Thr Leu
1665                1670                1675                1680
Ser Pro Ala Pro Asp Cys Ser Gln Pro Leu Asp Val Ile Leu Leu Leu
            1685                1690                1695
Asp Gly Ser Ser Ser Phe Pro Ala Ser Tyr Phe Asp Glu Met Lys Ser
        1700                1705                1710
Phe Ala Lys Ala Phe Ile Ser Lys Ala Asn Ile Gly Pro Arg Leu Thr
    1715                1720                1725
Gln Val Ser Val Leu Gln Tyr Gly Ser Ile Thr Thr Ile Asp Val Pro
        1730                1735                1740
Trp Asn Val Val Pro Glu Lys Ala His Leu Leu Ser Leu Val Asp Val
1745                1750                1755                1760
Met Gln Arg Glu Gly Gly Pro Ser Gln Ile Gly Asp Ala Leu Gly Phe
            1765                1770                1775
Ala Val Arg Tyr Leu Thr Ser Glu Met His Gly Ala Arg Pro Gly Ala
        1780                1785                1790
Ser Lys Ala Val Val Ile Leu Val Thr Asp Val Ser Val Asp Ser Val
    1795                1800                1805
Asp Ala Ala Ala Asp Ala Ala Arg Ser Asn Arg Val Thr Val Phe Pro
    1810                1815                1820
Ile Gly Ile Gly Asp Arg Tyr Asp Ala Ala Gln Leu Arg Ile Leu Ala
1825                1830                1835                1840
Gly Pro Ala Gly Asp Ser Asn Val Val Lys Leu Gln Arg Ile Glu Asp
            1845                1850                1855
Leu Pro Thr Met Val Thr Leu Gly Asn Ser Phe Leu His Lys Leu Cys
        1860                1865                1870
Ser Gly Phe Val Arg Ile Cys Met Asp Glu Asp Gly Asn Glu Lys Arg
    1875                1880                1885
Pro Gly Asp Val Trp Thr Leu Pro Asp Gln Cys His Thr Val Thr Cys
    1890                1895                1900
Gln Pro Asp Gly Gln Thr Leu Leu Lys Thr His Arg Val Asn Cys Asp
1905                1910                1915                1920
Arg Gly Leu Arg Pro Ser Cys Pro Asn Ser Gln Ser Pro Val Lys Val
            1925                1930                1935
Glu Glu Thr Cys Gly Cys Arg Trp Thr Cys Pro Cys Val Cys Thr Gly
        1940                1945                1950
Ser Ser Thr Arg His Ile Val Thr Phe Asp Gly Gln Asn Phe Lys Leu
    1955                1960                1965
Thr Gly Ser Cys Ser Tyr Val Leu Phe Gln Asn Lys Glu Gln Asp Leu
    1970                1975                1980
Glu Val Ile Leu His Asn Gly Ala Cys Ser Pro Gly Ala Arg Gln Gly
1985                1990                1995                2000
Cys Met Lys Ser Ile Glu Val Lys His Ser Ala Leu Ser Val Glu Leu
        2005                2010                2015
His Ser Asp Met Glu Val Thr Val Asn Gly Arg Leu Val Ser Val Pro
        2020                2025                2030
Tyr Val Gly Gly Asn Met Glu Val Asn Val Tyr Gly Ala Ile Met His
    2035                2040                2045
```

```
Glu Val Arg Phe Asn His Leu Gly His Ile Phe Thr Phe Thr Pro Gln
    2050                2055                2060

Asn Asn Glu Phe Gln Leu Gln Leu Ser Pro Lys Thr Phe Ala Ser Lys
2065                2070                2075                2080

Thr Tyr Gly Leu Cys Gly Ile Cys Asp Glu Asn Gly Ala Asn Asp Phe
            2085                2090                2095

Met Leu Arg Asp Gly Thr Val Thr Thr Asp Trp Lys Thr Leu Val Gln
        2100                2105                2110

Glu Trp Thr Val Gln Arg Pro Gly Gln Thr Cys Gln Pro Ile Leu Glu
        2115                2120                2125

Glu Gln Cys Leu Val Pro Asp Ser Ser His Cys Gln Val Leu Leu Leu
    2130                2135                2140

Pro Leu Phe Ala Glu Cys His Lys Val Leu Ala Pro Ala Thr Phe Tyr
    2145                2150                2155                2160

Ala Ile Cys Gln Gln Asp Ser Cys His Gln Glu Gln Val Cys Glu Val
            2165                2170                2175

Ile Ala Ser Tyr Ala His Leu Cys Arg Thr Asn Gly Val Cys Val Asp
        2180                2185                2190

Trp Arg Thr Pro Asp Phe Cys Ala Met Ser Cys Pro Pro Ser Leu Val
        2195                2200                2205

Tyr Asn His Cys Glu His Gly Cys Pro Arg His Cys Asp Gly Asn Val
    2210                2215                2220

Ser Ser Cys Gly Asp His Pro Ser Glu Gly Cys Phe Cys Pro Pro Asp
2225                2230                2235                2240

Lys Val Met Leu Glu Gly Ser Cys Val Pro Glu Glu Ala Cys Thr Gln
            2245                2250                2255

Cys Ile Gly Glu Asp Gly Val Gln His Gln Phe Leu Glu Ala Trp Val
        2260                2265                2270

Pro Asp His Gln Pro Cys Gln Ile Cys Thr Cys Leu Ser Gly Arg Lys
        2275                2280                2285

Val Asn Cys Thr Thr Gln Pro Cys Pro Thr Ala Lys Ala Pro Thr Cys
    2290                2295                2300

Gly Leu Cys Glu Val Ala Arg Leu Arg Gln Asn Ala Asp Gln Cys Cys
2305                2310                2315                2320

Pro Glu Tyr Glu Cys Val Cys Asp Pro Val Ser Cys Asp Leu Pro Pro
            2325                2330                2335

Val Pro His Cys Glu Arg Gly Leu Gln Pro Thr Leu Thr Asn Pro Gly
        2340                2345                2350

Glu Cys Arg Pro Asn Phe Thr Cys Ala Cys Arg Lys Glu Glu Cys Lys
        2355                2360                2365

Arg Val Ser Pro Pro Ser Cys Pro Pro His Arg Leu Pro Thr Leu Arg
    2370                2375                2380

Lys Thr Gln Cys Cys Asp Glu Tyr Glu Cys Ala Cys Asn Cys Val Asn
2385                2390                2395                2400

Ser Thr Val Ser Cys Pro Leu Gly Tyr Leu Ala Ser Thr Ala Thr Asn
            2405                2410                2415

Asp Cys Gly Cys Thr Thr Thr Thr Cys Leu Pro Asp Lys Val Cys Val
            2420                2425                2430

His Arg Ser Thr Ile Tyr Pro Val Gly Gln Phe Trp Glu Glu Gly Cys
        2435                2440                2445

Asp Val Cys Thr Cys Thr Asp Met Glu Asp Ala Val Met Gly Leu Arg
    2450                2455                2460
```

```
Val Ala Gln Cys Ser Gln Lys Pro Cys Glu Asp Ser Cys Arg Ser Gly
2465                2470                2475                2480

Phe Thr Tyr Val Leu His Glu Gly Glu Cys Cys Gly Arg Cys Leu Pro
            2485                2490                2495

Ser Ala Cys Glu Val Val Thr Gly Ser Pro Arg Gly Asp Ser Gln Ser
        2500                2505                2510

Ser Trp Lys Ser Val Gly Ser Gln Trp Ala Ser Pro Glu Asn Pro Cys
    2515                2520                2525

Leu Ile Asn Glu Cys Val Arg Val Lys Glu Glu Val Phe Ile Gln Gln
2530                2535                2540

Arg Asn Val Ser Cys Pro Gln Leu Glu Val Pro Val Cys Pro Ser Gly
2545                2550                2555                2560

Phe Gln Leu Ser Cys Lys Thr Ser Ala Cys Cys Pro Ser Cys Arg Cys
            2565                2570                2575

Glu Arg Met Glu Ala Cys Met Leu Asn Gly Thr Val Ile Gly Pro Gly
            2580                2585                2590

Lys Thr Val Met Ile Asp Val Cys Thr Thr Cys Arg Cys Met Val Gln
            2595                2600                2605

Val Gly Val Ile Ser Gly Phe Lys Leu Glu Cys Arg Lys Thr Thr Cys
    2610                2615                2620

Asn Pro Cys Pro Leu Gly Tyr Lys Glu Asn Asn Thr Gly Glu Cys
2625                2630                2635                2640

Cys Gly Arg Cys Leu Pro Thr Ala Cys Thr Ile Gln Leu Arg Gly Gly
            2645                2650                2655

Gln Ile Met Thr Leu Lys Arg Asp Glu Thr Leu Gln Asp Gly Cys Asp
            2660                2665                2670

Thr His Phe Cys Lys Val Asn Glu Arg Gly Glu Tyr Phe Trp Glu Lys
            2675                2680                2685

Arg Val Thr Gly Cys Pro Pro Phe Asp Glu His Lys Cys Leu Ala Glu
            2690                2695                2700

Gly Gly Lys Ile Met Lys Ile Pro Gly Thr Cys Cys Asp Thr Cys Glu
2705                2710                2715                2720

Glu Pro Glu Cys Asn Asp Ile Thr Ala Arg Leu Gln Tyr Val Lys Val
            2725                2730                2735

Gly Ser Cys Lys Ser Glu Val Glu Val Asp Ile His Tyr Cys Gln Gly
            2740                2745                2750

Lys Cys Ala Ser Lys Ala Met Tyr Ser Ile Asp Ile Asn Asp Val Gln
            2755                2760                2765

Asp Gln Cys Ser Cys Cys Ser Pro Thr Arg Thr Glu Pro Met Gln Val
    2770                2775                2780

Ala Leu His Cys Thr Asn Gly Ser Val Val Tyr His Glu Val Leu Asn
2785                2790                2795                2800

Ala Met Glu Cys Lys Cys Ser Pro Arg Lys Cys Ser Lys
            2805                2810

<210> SEQ ID NO 2
<211> LENGTH: 210
<212> TYPE: PRT
<213> ORGANISM: Homo sapiens

<400> SEQUENCE: 2

Asp Leu Ala Pro Glu Ala Pro Pro Thr Leu Pro Pro His Met Ala
 1               5                  10                  15

Gln Val Thr Val Gly Pro Gly Leu Leu Gly Val Ser Thr Leu Gly Pro
            20                  25                  30
```

Lys Arg Asn Ser Met Val Leu Asp Val Ala Phe Val Leu Glu Gly Ser
           35                  40                  45

Asp Lys Ile Gly Glu Ala Asp Phe Asn Arg Ser Lys Glu Phe Met Glu
 50                  55                  60

Glu Val Ile Gln Arg Met Asp Val Gly Gln Asp Ser Ile His Val Thr
 65                  70                  75                  80

Val Leu Gln Tyr Ser Tyr Met Val Thr Val Glu Tyr Pro Phe Ser Glu
                 85                  90                  95

Ala Gln Ser Lys Gly Asp Ile Leu Gln Arg Val Arg Glu Ile Arg Tyr
            100                 105                 110

Gln Gly Gly Asn Arg Thr Asn Thr Gly Leu Ala Leu Arg Tyr Leu Ser
        115                 120                 125

Asp His Ser Phe Leu Val Ser Gln Gly Asp Arg Glu Gln Ala Pro Asn
    130                 135                 140

Leu Val Tyr Met Val Thr Gly Asn Pro Ala Ser Asp Glu Ile Lys Arg
145                 150                 155                 160

Leu Pro Gly Asp Ile Gln Val Val Pro Ile Gly Val Gly Pro Asn Ala
                165                 170                 175

Asn Val Gln Glu Leu Glu Arg Ile Gly Trp Pro Asn Ala Pro Ile Leu
            180                 185                 190

Ile Gln Asp Phe Glu Thr Leu Pro Arg Glu Ala Pro Asp Leu Val Leu
        195                 200                 205

Gln Arg
    210

<210> SEQ ID NO 3
<211> LENGTH: 115
<212> TYPE: PRT
<213> ORGANISM: Homo sapiens

<400> SEQUENCE: 3

Glu Ala Gln Ser Lys Gly Asp Ile Leu Gln Arg Val Arg Glu Ile Arg
 1               5                  10                  15

Tyr Gln Gly Gly Asn Arg Thr Asn Thr Gly Leu Ala Leu Arg Tyr Leu
             20                  25                  30

Ser Asp His Ser Phe Leu Val Ser Gln Gly Asp Arg Glu Gln Ala Pro
         35                  40                  45

Asn Leu Val Tyr Met Val Thr Gly Asn Pro Ala Ser Asp Glu Ile Lys
     50                  55                  60

Arg Leu Pro Gly Asp Ile Gln Val Val Pro Ile Gly Val Gly Pro Asn
 65                  70                  75                  80

Ala Asn Val Gln Glu Leu Glu Arg Ile Gly Trp Pro Asn Ala Pro Ile
                 85                  90                  95

Leu Ile Gln Asp Phe Glu Thr Leu Pro Arg Glu Ala Pro Asp Leu Val
            100                 105                 110

Leu Gln Arg
        115

<210> SEQ ID NO 4
<211> LENGTH: 82
<212> TYPE: PRT
<213> ORGANISM: Homo sapiens

<400> SEQUENCE: 4

Asp His Ser Phe Leu Val Ser Gln Gly Asp Arg Glu Gln Ala Pro Asn
 1               5                  10                  15

```
Leu Val Tyr Met Val Thr Gly Asn Pro Ala Ser Asp Glu Ile Lys Arg
            20                  25                  30

Leu Pro Gly Asp Ile Gln Val Val Pro Ile Gly Val Gly Pro Asn Ala
        35                  40                  45

Asn Val Gln Glu Leu Glu Arg Ile Gly Trp Pro Asn Ala Pro Ile Leu
    50                  55                  60

Ile Gln Asp Phe Glu Thr Leu Pro Arg Glu Ala Pro Asp Leu Val Leu
65                  70                  75                  80

Gln Arg

<210> SEQ ID NO 5
<211> LENGTH: 73
<212> TYPE: PRT
<213> ORGANISM: Homo sapiens

<400> SEQUENCE: 5

Asp Arg Glu Gln Ala Pro Asn Leu Val Tyr Met Val Thr Gly Asn Pro
1               5                   10                  15

Ala Ser Asp Glu Ile Lys Arg Leu Pro Gly Asp Ile Gln Val Val Pro
            20                  25                  30

Ile Gly Val Gly Pro Asn Ala Asn Val Gln Glu Leu Glu Arg Ile Gly
        35                  40                  45

Trp Pro Asn Ala Pro Ile Leu Ile Gln Asp Phe Glu Thr Leu Pro Arg
    50                  55                  60

Glu Ala Pro Asp Leu Val Leu Gln Arg
65                  70

<210> SEQ ID NO 6
<211> LENGTH: 64
<212> TYPE: PRT
<213> ORGANISM: Homo sapiens

<400> SEQUENCE: 6

Asp Arg Glu Gln Ala Pro Asn Leu Val Tyr Met Val Thr Gly Asn Pro
1               5                   10                  15

Ala Ser Asp Glu Ile Lys Arg Leu Pro Gly Asp Ile Gln Val Val Pro
            20                  25                  30

Ile Gly Val Gly Pro Asn Ala Asn Val Gln Glu Leu Glu Arg Ile Gly
        35                  40                  45

Trp Pro Asn Ala Pro Ile Leu Ile Gln Asp Phe Glu Thr Leu Pro Arg
    50                  55                  60

<210> SEQ ID NO 7
<211> LENGTH: 30
<212> TYPE: DNA
<213> ORGANISM: Artificial Sequence
<220> FEATURE:
<223> OTHER INFORMATION: A sense primer used in RT-PCR for obtaining
      Asp1459-Arg1668 region of mature human VWF subunit

<400> SEQUENCE: 7
cgggatccga ccttgccct gaagcccctc                                           30

<210> SEQ ID NO 8
<211> LENGTH: 51
<212> TYPE: DNA
<213> ORGANISM: Artificial Sequence
<220> FEATURE:
<223> OTHER INFORMATION: An anti-sense primer used in RT-PCR for
      obtaining Asp1459-Arg1668 region of mature human VWF subunit
```

-continued

```
<400> SEQUENCE: 8
cggaattctc agtgatggtg atggtgatgc ctctgcagca ccaggtcagg a         51

<210> SEQ ID NO 9
<211> LENGTH: 30
<212> TYPE: DNA
<213> ORGANISM: Artificial Sequence
<220> FEATURE:
<223> OTHER INFORMATION: A sense primer used in RT-PCR for obtaining
      Glu1554-Arg1668,Asp1587-Arg1668,Asp1596-Arg1668, and
      Asp1596-Arg1659 regions of mature human VWF subunit

<400> SEQUENCE: 9
cgggatccga ggcacagtcc aaaggggaca                                 30

<210> SEQ ID NO 10
<211> LENGTH: 30
<212> TYPE: DNA
<213> ORGANISM: Artificial Sequence
<220> FEATURE:
<223> OTHER INFORMATION: A sense primer used in RT-PCR for obtaining
      Glu1554-Arg1668,Asp1587-Arg1668,Asp1596-Arg1668, and
      Asp1596-Arg1659 regions of mature human VWF subunit

<400> SEQUENCE: 10
cgggatccga ccacagcttc ttggtcagcc                                 30

<210> SEQ ID NO 11
<211> LENGTH: 30
<212> TYPE: DNA
<213> ORGANISM: Artificial Sequence
<220> FEATURE:
<223> OTHER INFORMATION: A sense primer used in RT-PCR for obtaining
      Glu1554-Arg1668,Asp1587-Arg1668,Asp1596-Arg1668, and
      Asp1596-Arg1659 regions of mature human VWF subunit

<400> SEQUENCE: 11
cgggatccga ccgggagcag gcgcccaacc                                 30

<210> SEQ ID NO 12
<211> LENGTH: 51
<212> TYPE: DNA
<213> ORGANISM: Artificial Sequence
<220> FEATURE:
<223> OTHER INFORMATION: An anti-sense primer used in RT-PCR for
      obtaining Glu1554-Arg1668,Asp1587-Arg1668,Asp1596-Arg1668, and
      Asp1596-Arg1659 regions of mature human VWF subunit

<400> SEQUENCE: 12
cggaattctc agtgatggtg atggtgatgt cggggagcg tctcaaagtc c          51
```